United States Patent [19]

van Anholt et al.

[11] 4,196,241
[45] Apr. 1, 1980

[54] INTERTWINED CARPET YARN OF VARYING DYE AFFINITY AND CARPETS MADE FROM SAID YARN

[75] Inventors: Willem C. van Anholt, Arnhem; Antonie De Geus, PC Velp, both of Netherlands

[73] Assignee: Akzona Incorporated, Asheville, N.C.

[21] Appl. No.: 2,120

[22] Filed: Jan. 9, 1979

[30] Foreign Application Priority Data

Oct. 1, 1978 [NL] Netherlands .................... 7800277

[51] Int. Cl.² .................................. D02G 3/00
[52] U.S. Cl. .................................. 428/92; 57/239; 57/245; 57/247; 428/97; 428/367; 428/369; 428/370; 428/371
[58] Field of Search ............... 428/92, 97, 367, 369, 428/370, 371; 57/205, 208, 239, 245, 247

[56] References Cited

U.S. PATENT DOCUMENTS 3,461,024 8/1969 Bloch ................................ 428/97

Primary Examiner—Marion E. McCamish
Attorney, Agent, or Firm—Francis W. Young; Tom R. Vestal

[57] ABSTRACT

The invention relates to a composite, synthetic multifilament carpet yarn of polyamide, which yarn is composed of a number of intertwined basic yarns of varying dye affinity and/or crimped yarns of different colors.

7 Claims, 8 Drawing Figures

INTERTWINED CARPET YARN OF VARYING DYE AFFINITY AND CARPETS MADE FROM SAID YARN

It is known in U.S. Pat. No. 3,479,810 to make carpet yarns from a number of intertwined basic yarns of varying dye affinity. These yarns, when dyed, produce a composite yarn having differing color variations along its length as the result of their intertwinement.

It is also known to combine the basic yarns after they are dyed and intertwine them to produce the same result. Carpets made from these yarns present a heather appearance and find wide acceptance in the market place.

After extensive testing, a carpet yarn of this type with especially favorable characteristics in terms of hand, appearance, thermal insulation, covering power, wear resistance and color gradation has now been found. The yarn of the invention is characterized in that the composite yarn has a total denier of 3000 to 50,000 dtex, the crimp contraction of the composite yarns is below about 20%, the number of crimp waves per yarn—that is the number of filament portions protruding from the yarn body recorded over a length of 5 meters—is at least 200 when measured at a distance of 1 millimeter from the compact yarn body. Further, the twist angle of the composite yarn varies on the average between 10° and 60°, whereby the dimensions of twist angles X measured in degrees varies so that twist angles X comply with a frequency distribution Y, which can be described by means of a model given by the formula:

$$Y = Y_0(X - X_{min})^{m1} \cdot (1 - \frac{X - X_{min}}{X_{max} - X_{min}})^{m2}$$

wherein the parameters may vary as follows:

$0° \leq X_{min} \leq 10°$   $-0.3 \leq m_1 \leq 10$
$20° \leq X_{max} \leq 80°$   $1 \leq m_2 \leq 10$ This model is based on a Type 1 model of the Karl Pearson system.

The composite yarn possesses externally a first group of filaments with less pronounced differences in dye affinity and/or color, and at least a second group with relatively pronounced deviations in dye affinity and/or color differences or spots whereby, for the dye affinity and/or color differences of the second group, looked at from one side on the surface of the yarn and along the yarn, the lengths a of these differences measured in millimeters vary to such an extend that the lengths a comply with a frequency distribution b, which can be expressed by the formula:

$$b = b_0(a - a_{min})^{m1} \cdot (1 - \frac{a - a_{min}}{a_{max} - a_{min}})^{m2}$$

in which the parameters may vary as follows:

$0 \leq a_{min} \leq 10mm$   $-0.3 \leq m_1 \leq 10$
$20 \leq a_{max} \leq 30mm$   $1 \leq m_2 \leq 10$ and whereby for the dye affinity and/or color differences of the second group, seen from one side on the surface of the yarn and along the yarn, the mutual center distances p of these differences measured in mm, vary to such an extent that the center distances p comply with a frequency distribution q which can be expressed by the formula:

$$q = q_0(p - p_{min})^{m1} \cdot (1 - \frac{p - p_{min}}{p_{max} - p_{min}})^{m2}$$

in which the parameters may vary as follows:

$0 \leq p_{mm} \leq 15mm$
$25 \leq p_{max} \leq 300mm$
$-0.3 \leq m_1 \leq 10$
$1 \leq m_2 \leq 10$ The carpet yarn of the invention exhibits, surprisingly, characteristics surpassing those of better woolen carpet yarns, whereas the typical advantages of a synthetic yarn, such as high chemical and soiling resistance, ease of care, wear strength and the like are retained. The composite carpet yarn according to the invention is preferably characterized in that the denier of the yarn is 5000 to 20,000 dtex, the crimp contraction is 10% to 18%, the number of crimp waves per centimeter is 3 to 5, and the average twist angle is 15% to 40%.

The *crimp contraction* is measured as follows. The latent crimp is first developed in a skein of the composite yarn by immersing said yarn skein for 1 minute without tension in water at 98° C. After drying at 50° C. and subsequent conditioning at 20° C. and 65% RH, the length $L_1$ of the skein is measured under a load of 0.02 cN/tex. Subsequently, the stretched length $L_2$ of the same skein is measured at a load of 2 cN/tex. The mentioned crimp contraction is then calculated by means of the formula $(L_2 - L_1/L_2) \times 100\%$.

The *number of crimp waves per centimeter* is determined as follows. At least 30 specimens of yarn measuring 3 cm in length, which length was determined under a load of 2 cN/tex, are sampled at random from the composite yarn, after developing the latent crimp in the above described manner. These selected yarn samples are mounted in a frame and magnified on a projector to count the number N of crimp waves. The average number of crimp waves per cm is then calculated by means of the formula $N/(30 \times 3)$ crimp waves/cm.

The *twist angle* is measured as follows. The stretched composite yarn is mounted on a piece of paper and a line is drawn parallel to the longitudinal axis of the yarn. A protractor is then used to measure twist angles $X_1$, $X_2$, $X_3$, $X_4$, etc. These data are used to calculate the average twist angle and distribution parameters. As found after statistical processing of the measuring results, the dimensions of the twist angle X measured in degrees vary to such extent that the twist angles X comply with a frequency distribution Y, which can be described by the model mentioned above.

DETAILED DESCRIPTION OF THE INVENTION

Figure 1:
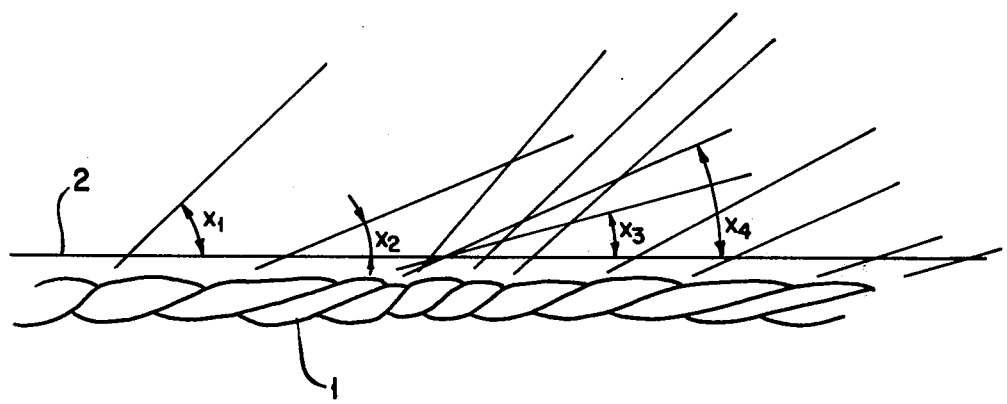
FIG. 1 shows a length of composite yarn depicting twist angle measurement.

A sample of yarn 1 shown in FIG. 1 is treated according to the crimp contraction first described above, then mounted on a piece of paper and a line 2 is drawn parallel to the longitudinal axis of the yarn 1.

The first angles $X_1$, $X_2$, $X_3$, $X_4$, etc are represented in FIG. 1.

Figure 2:
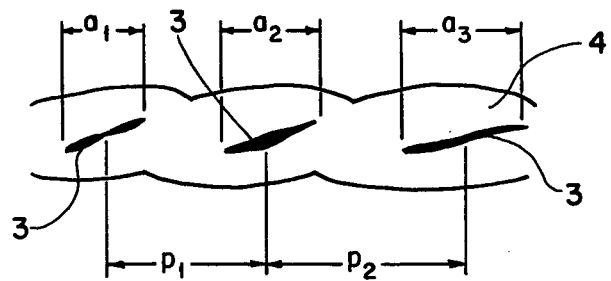
FIG. 2 depicts the frequency distribution of dye affinity differences along the length of the present yarn.

The composite yarn of the invention possesses externally different dye affinity and/or color differences or spots that can be divided into two groups. The differences or spots of the first group are less pronounced but their number is very large. The differences or spots of the second group are much smaller in number than those of the first group, but the differences or spots in the second group are much more pronounced than those in the first group. The differences or spots 3 of the second group of the dyed, composite yarn 4 were subjected to a number of measurements, explained by referring to FIG. 2. In FIG. 2, the composite yarn is shown to have a number of dark, oblong, slanted spots 3 representing the mentioned sharp color differences or spots of the second group. The composite dyed yarn is placed under tension on a board. Subsequently, using a ruler, the lengths $a_1$, $a_2$, $a_3$, etc. of the color spots are measured. In fact, this measures the projection of the length of the color spots. However, these projections will be used below as length a. As statistical analysis of the measurements has indicated, lengths a of these color spots vary so that said lengths a, measured in millimeters comply with a frequency distribution b, which can be described by means of a model according to Type I of the Karl Pearson system, mentioned above.

Figure 3:
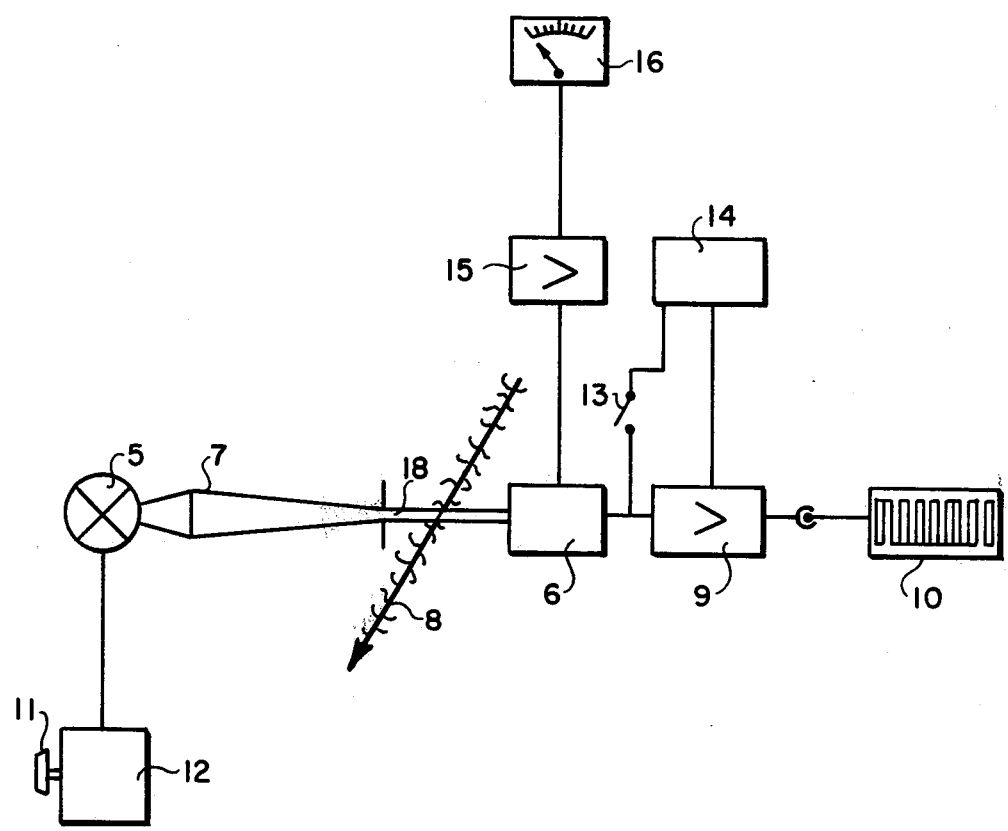
FIG. 3 is a schematical diagram of a device used to measure the hairiness of the composite yarn.

FIG. 3 shows a schematic of the device used to measure the hairiness of the composite yarn. As shown in FIG. 3, the light of a lamp 5 is converted by a "Axicon" lens to a small bundle of parallel light beams. The diameter of the light beam is about 0.5 mm. The light beam 4 impinges on a photo transistor 6. This photo transistor emits an electrical signal determined by the amount of incident light. Between lens 7 and photo transistor 6 is located yarn 8, whose hairiness must be measured. The axis of yarn and light beam intersect perpendicularly and the distance between yarn surface and light bundle can be adjusted. Yarn 8 is advanced by means of a guide system at a rate of 30 m/min and a tension of 0.2 cN/tex. A filament of the yarn interrupting the light beam changes the electrical signal and this impulse is amplified by amplifier 9 and counted by electronic counter 10. The hairiness meter is of a known type and conventionally equipped with an adjusting knob 11 for the light intensity, and light intensity, and input lamp 12, a calibrating switch 13, an input amplifier 14, an amplifier 15 and a meter 16 for the light intensity. The distance between yarn surface and light beam can be adjusted (not shown) by means of a micrometer screw connected to the yarn guiding system. To adjust the distance between yarn surface, i.e. the edge of the compact yarn body, and light beam use is made of the point at which the center of the yarn core or of the yarn body intersects the center of the light beam. This point can be determined for each yarn on the apparatus, because the amount of transmitted light is minimal. The yarn is then raised by means of the micrometer screw until the desired distance between the center of the light beam and the edge of the yarn core is obtained.

Figure 4:
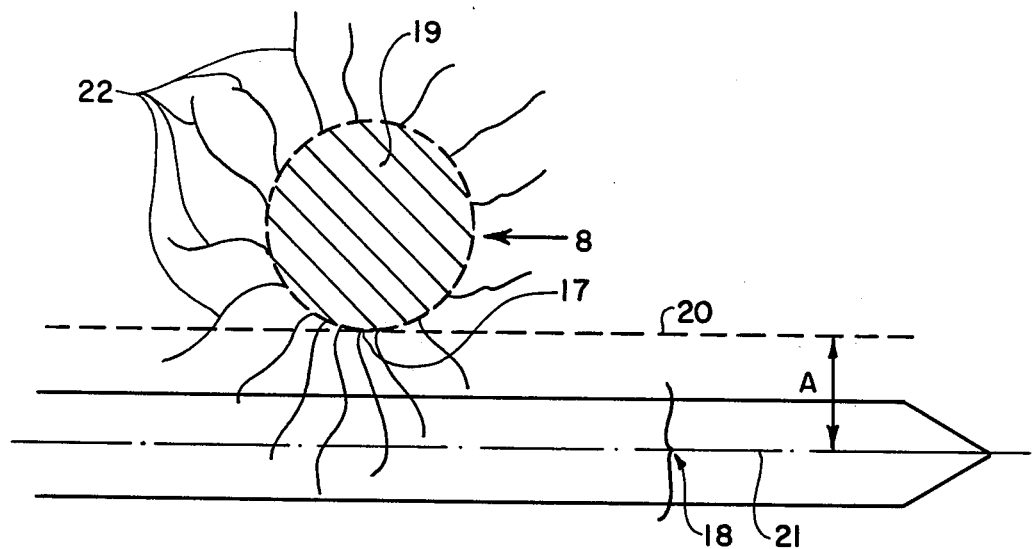
FIGS. 4 and 5 schematically illustrate the differences in measurement of hairiness at different distances from the composite yarn core.
Figure 5:
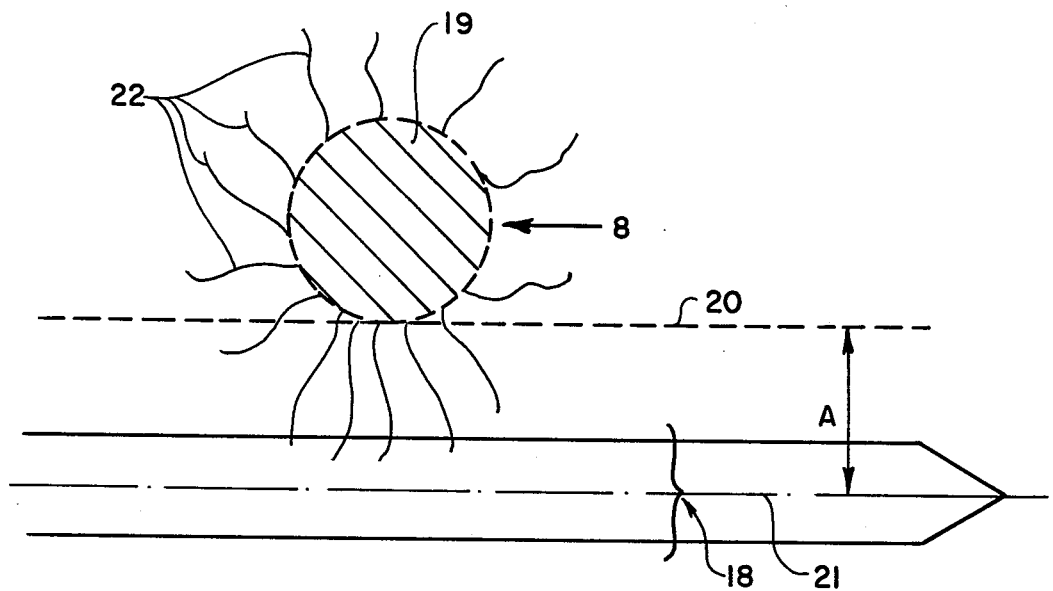

As follows from the preceding description of the hairiness meter, this measurement counts only the hairs or filament portions intersection a flat plane located at a distance A from the yarn surface, i.e. from the edge 17 of the compact yarn body 8. This is further illustrated on hand of schematic drawings FIGS. 4 and 5. In FIGS. 4 and 5, yarn 8 is shown in cross section and the light beam 18 in longitudinal section. Reference number 19 identifies the core of the compact yarn body; 22 the hairs protruding from the compact yarn body. The above mentioned edge of the compact yarn body is identified by contact line 20, whereas the axis of the light beam is identified by reference number 21.

FIGS. 4 and 5 are not drawn to scale and differ only in that the mentioned distances A are different. FIG. 4 schematically illustrates the situation whereby the distance A=1 mm, whereas in FIG. 5 distance A=4.0 mm. As furthermore shown in FIGS. 4 and 5, the distances A are measured from the center 21 of the measuring light beam to the nearest edge 20 of the almost compact yarn body 19. In certain cases, a hair will just end in the light beam and may or may not be counted, depending upon the electric impulse being generated. The number of counted hairs N per 5 meter length of the yarn is referred to in the description and in the claims as the hairiness of the yarn, whereby N represents the average of 5 measurements. It is obvious that the hairiness N will depend, among other things, upon:

a. The distance over which the hairs 22 protrude from the core and the distance A from the center 21 of the light beam 18 to the edge 20 of the compact yarn body
b. The number of hairs per unit length of the yarn
c. The hair's shape.

EXAMPLE

Figure 6:
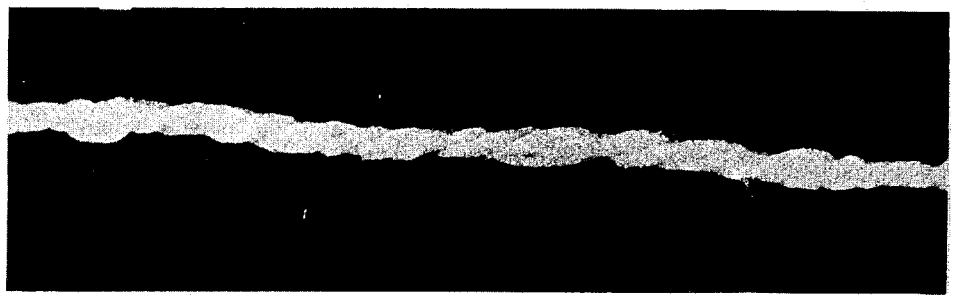
FIGS. 6 to 8 are photographs of yarn of the invention.
Figure 7:
Figure 8:
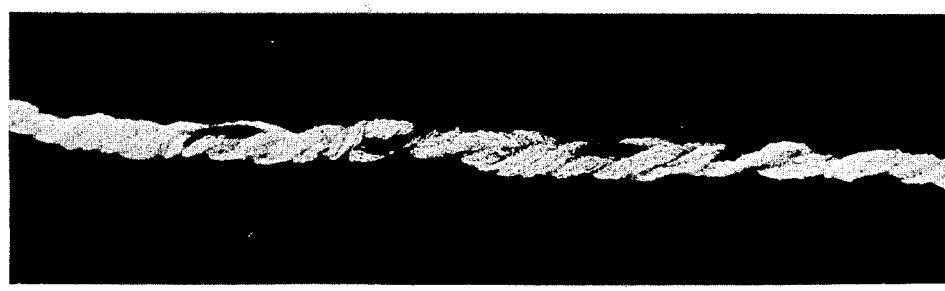

An example of the carpet yarn according to the invention is shown at a magnification of 2 in FIGS. 6, 7, and 8.

FIG. 6 illustrates the differential dyeing yarn before dyeing, in which the yarn has a uniform white color.

FIGS. 7 and 8 show different lengths of the same yarn after dyeing. Although this yarn exhibits a first group with less pronounced color differences, because of the relatively light colors being used they cannot be distinguished on the black/white photograph and are represented in fact by all white portions on FIGS. 7 and 8. The yarn possesses a second group with relatively sharp color differences or color spots, which are indeed identifiable on FIGS. 7 and 8, namely in the form of clearly visible dark spots in the yarn shown in FIGS. 7 and 8. FIG. 7 indicates how length a and center distance p of these dark spots can be measured. All three photos clearly show the variations in the size of twist angles X along the yarn. Measurements of the yarn according to this example indicate that with the Pearson formula, the frequency distribution Y of the twist angles X is determined by using as parameters the following values:

$X_{min} = 0°$;
$X_{max} = 80°$;
$m_1 = 0.67$;
$m_2 = 2.24$.

The frequency distribution b for the cited lengths a of the color spots of the second group can be determined for the yarn according to this example by means of the Pearson formula with the following parameters:

$a_{min} = 0$ mm;
$x_{max} = 20$ mm;
$m_1 = 1.36$;
$m_2 = 4.83$.

The frequency distribution q for the cited center distances p of the color spots of the second group can also be determined for the yarn of the example according to Pearson's formula by means of the following parameters:

$p_{min} = 0$ mm;
$p_{max} = 80$ mm;
$m_1 = 0.78$;
$m_2 = 3.68$.

The composite yarn according to the example shown in FIGS. 7 and 8 has a total denier of approximately 18,000 dtex and a total of 864 individual filaments. The composite yarn consists of three basic yarns, each being approximately 6000 dtex and 288 filaments. Each basic yarn is in turn composed of three yarn segments, each being about 2000 dtex and 96 filaments. Each segment yarn is in turn composed of three units, each being approximately the same denier and comprising 32 filaments. Consequently, each basic yarn comprises 3×3 unit yarns and the composite end yarn comprises (3×3)×3=27 unit yarns.

Each basic yarn comprises yarn segments of the following composition:

The first yarn segment consists of 2 regular acid dyeing nylon 6 yarn units of 1 basic dyeing nylon 6 yarn units (RRB). The second yard segment consists of 1 regular acid dyeing nylon 6 yarn unit, 1 low acid dyeing nylon 6 yarn and 1 deep acid dyeing nylon 6 yarn (RLD). The third yarn segment consists of 1 regular acid dyeing nylon 6 yarn, 1 low acid dyeing nylon 6 yarn and 1 deep dyeing nylon 6 yarn (RLD).

The segment yarns are textured by means of any of the conventional texturing processes, such as blowing by means of a heated or unheated fluid under pressure, e.g. air or steam, whereby the filaments are more or less tangled or intermingled. From three of the above mentioned yarn segments a basic yarn according to this version is obtained by twisting the three segment yarns in a "Z" direction 50 turns per meter. Three identical basic yarns are twisted at 50 turns per meter in an "S" direction to a composite yarn. The twist uniformity of the resulting yarn is disrupted and the surface is uneven and rough. The cited presence of low (L), regular (R) and deep (D) acid dyeable yarn units produces the mentioned first group of low dye affinity and/or color differences in the composite end yarn. The cited presence of the small number of three basic (B) dyeing yarn units produces the cited second group of pronounced dye affinity and/or color differences or spots in the composite end yarn, which, as described, are visible in FIGS. 7 and 8.

In the above described example of the composite yarn according to the invention, the hairiness was approximately 400 at a distance A=1.0 mm from the compact yarn core, whereas at a distance A=4.0 mm the hairiness was approximately 100. Furthermore, the yarn according to the example had a crimp contraction of 15% and 3.5 crimp waves per cm. The basic yarns of the yarn according to the example had a tridimensional crimp.

In the described version the color effects are only produced in the yarn or in the carpet by means of piece-dyeing, because a composite yarn of differential dyeing components is being used as starting material. In principle, this effect can also be achieved by using as starting material spun-dyed yarns of different colors or by creating color effects by means of color printing techniques.

Various modifications are possible within the framework of the invention. For instance, the composite yarn can be treated with an antistatic agent by any of different known methods. The cross section of the filaments of the yarn can be circular or non-circular, lobed or polygonal. Moreover, the composite yarn according to the invention may comprise individual filaments of varying deniers.

What is claimed is:

1. A composite synthetic multifilament carpet yarn, comprising at least two intertwined outside groups of differentially colorable crimped basic yarns, the composite yarns having a denier of 3000 to 50,000 dtex, a crimp contraction of less than about 20%, a number of crimp waves per cm of less than about 6, a hairiness of about at least 200 when measured over a length of 5 meters at a distance of 1.0 mm from the compact yarn body, a varying twist angle averaging from between about 10° to 60° whereby the dimensions of the twist angles X, measured in degrees, comply with a frequency distribution Y, according to the formula:

$$Y = Y_0(X - X_{min})^{m_1} \cdot (1 - \frac{X - X_{min}}{X_{max} - X_{min}})^{m_2}$$

in which:

$0° \leq X_{min} \leq 10°$  $-0.3 \leq m_1 \leq 10$
$20° \leq X_{max} \leq 80°$  $1 \leq m_2 \leq 10$ said first outside group having less pronounced differences in color and said second outside group having relatively more sharply deviating color differences, the length of the differences a in millimeters as seen from one side of the yarn surface having a frequency distribution b expressed according to the formula:

$$b = b_0(a - a_{min})^{m_1} \cdot (1 - \frac{a - a_{min}}{a_{max} - a_{min}})^{m_2}$$

wherein:

$0 \leq a_{min} \leq 10$ mm  $-0.3 \leq m_1 \leq 10$
$20 \leq a_{max} \leq 30$ mm  $1 \leq m_2 \leq 10$ and the distance p in millimeters between the color differences having a frequency distribution q expressed according to the formula:

$$q = q_0(p - p_{min})^{m_1} \cdot (1 - \frac{p - p_{min}}{p_{max} - p_{min}})^{m_2}$$

wherein:

$0 \leq p_{min} \leq 15$ mm  $-0.3 \leq m_1 \leq 10$
$25 \leq p_{max} \leq 300$ mm  $1 \leq m_2 \leq 10$ 2. Carpet yarn according to claim 1 wherein the composite yarn denier is between about 5000 to 20,000 dtex.

3. Carpet yarn according to claim 1 or 2 wherein the crimp contraction is between about 10% to 18%.

4. Carpet yarn according to claims 1, 2, or 3 wherein the number of crimp waves per centimeter is between about 3 to 5.

5. Carpet yarn according to claims 1, 2, 3, or 4 wherein the average twist angle is between about 15° to 40°.

6. Carpet yarn of claim 5 wherein the basic yarns have a tridimensional crimp.

7. A carpet made from the composite yarn of claim 6.

* * * * *